United States Patent [19]

Detweiler et al.

[11] 4,329,317

[45] May 11, 1982

[54] METHOD OF STABILIZING A SPECIMEN SLIDE FOR OCCULT BLOOD TESTING

[75] Inventors: Michael B. Detweiler, San Jose; Paul J. Lawrence, Campbell; Charles W. Townsley, San Jose, all of Calif.

[73] Assignee: Smithkline Instruments, Inc., Sunnyvale, Calif.

[21] Appl. No.: 229,430

[22] Filed: Jan. 29, 1981

[51] Int. Cl.³ ............................................. G01N 33/72
[52] U.S. Cl. .................................... 422/58; 23/230 B; 23/931; 23/932
[58] Field of Search ................... 23/230 B, 931, 932, 23/913; 422/58, 55, 56, 57

[56] References Cited

U.S. PATENT DOCUMENTS 3,252,762  5/1966  Adams, Jr. et al. .............. 23/931 X
3,853,471 12/1974  Rittersdorf et al. .............. 422/56 X
3,996,006 12/1976  Pagano ............................ 422/58 X
4,071,321  1/1978  Lam ..................................... 422/56

FOREIGN PATENT DOCUMENTS 2716060 10/1978  Fed. Rep. of Germany.

*Primary Examiner*—Arnold Turk
*Attorney, Agent, or Firm*—Joseph A. Marlino; Richard D. Foggio; Alan D. Lourie

[57] ABSTRACT

Specimen test slides for occult blood having a receiving sheet between a front panel and a rear panel with openings in the front and rear panels and pivotal covers coated with 2,6-di-tert-butyl-p-cresol to cover said openings.

6 Claims, No Drawings

METHOD OF STABILIZING A SPECIMEN SLIDE FOR OCCULT BLOOD TESTING

Specimen test slides and procedures for detecting occult blood in fecal matter are well known. For example, U.S. Pat. No. 3,996,006 discloses slides having a specimen receiving sheet between a front panel and a rear panel with openings in the front and rear panels and pivotal covers or flaps to cover these openings. One such test slide is sold under the trademark of 'Hemoccult'.

The specimen receiving sheet is generally an absorbent paper impregnated with a guaiac reagent. The hemoglobin catalyzed oxidation of the guaiac extract coated paper is used clinically to detect occult blood in feces. Briefly, the test procedure is as follows.

A sample of fecal matter is smeared onto the guaiac paper through an opening of the front panel. The panel is then covered and the flap of the rear panel is opened. A developing solution such as hydrogen peroxide is applied to the guaiac paper via the corresponding opening in the rear panel. If blood is present in the fecal matter, the guaiac reaction will color the paper blue. The overall reaction is as follows:

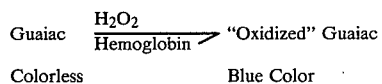

$$\text{Guaiac} \xrightarrow[\text{Hemoglobin}]{H_2O_2} \text{"Oxidized" Guaiac}$$

Colorless → Blue Color

One of the major disadvantages of the guaiac test is that premature blueing occurs in the guaiac impregnated paper. Occasionally the paper will turn a slight blue color upon exposure to air. Trace amounts of nitrogen dioxide, ozone, and other oxidants in the air can penetrate the closed slide and react with the guaiac in the paper to cause a blue coloration. This premature blueing can introduce an element of confusion in the test and result in false positive tests.

Previous attempts have been made to stabilize the guaiac impregnated paper. Some commercial test slides place glazine paper over the openings in the front panel to protect the guaiac paper when the slide is exposed to the atmosphere. German Offenlegungschrift No. 2,716,060 discloses a method of treating the paper with various antioxidants. The results of this test revealed that the paper treated at protective antioxidant concentrations was not useful in detecting pathological amounts of blood in feces because the sensitivity of the test was negatively influenced. When the concentrations of antioxidants were reduced so that a sufficient sensitivity of the test was reached, the substances lost their stabilizing action.

Offenlegungschrift No. 2,716,060 reported that of all the compounds tested, the 1-arylsemicarbazides, specifically 1-phenylsemicarbazide, gave some degree of protection when impregnated on the guaiac paper. However, 1-phenylsemicarbazide also increases the bleaching of the blue color produced in a positive test.

It is therefore the object of this invention to stabilize the guaiac impregnated paper by preventing premature blueing without essentially influencing the sensitivity of the test.

Unexpectedly, it was discovered that when 2,6-di-tert-butyl-p-cresol (BHT) was coated on the cover or flap of the slide and not impregnated in the guaiac paper, the paper was stable against premature blueing caused by light and air and pathological amounts of blood in feces were easily detectable.

Several major advantages result in coating the slide cover or container instead of impregnating the guaiac paper with the antioxidants. Due to the small concentration of antioxidant required, the material can be applied by dissolving and/or suspending it in the thin film of varnish that is normally employed to prevent ink smearing during manufacture. Further, once the antioxidant is added to the coating varnish there is no change in the manufacturing procedure. This approach is very cost effective. Most important, since no additional material is introduced into the guaiac paper, the performance of the slide remains unchanged.

A number of antioxidants were tested for their ability to prevent premature blueing of 'Hemoccult' slides by coating the slide, specifically the inside flap or cover. The test procedure was as follows:

Six antioxidants were dissolved in acetone, 22.5μ moles of each were then applied to the inside cover of the slides. After all the solvent evaporated the slides were closed to simulate an unopened 'Hemoccult' slide. The slides were then exposed to nitrogen dioxide in air, 2 ppm. The blueing time of each slide was noted. Following are the results:

| Compound | Blueing Time* |
|---|---|
| Control (acetone alone) | 5 minutes |
| Vanillin | " |
| 1-phenylsemicarbazide | " |
| 4-phenylsemicarbazide | " |
| 4-phenyl-3-thiosemicarbazide | " |
| 3,3-thiodipropionic acid | " |
| BHT | 240 minutes |

The results clearly demonstrate that under exaggerated conditions, when BHT is coated on the slide cover, the guaiac paper is protected against blueing. It will be noted that although 1-phenylsemicarbazide has been reported to give some degree of protection when applied directly to the guaiac paper, it has no effect when coated on the inside cover of the slide.

BHT was dissolved in varnish, applied to the inside cover of a slide and the closed slide exposed to air under normal conditions. Following are the results of this test:

| mg. BHT Applied | Blueing Time* |
|---|---|
| 0 | 2 days |
| 0.6 | 20 days |
| 1.5 | 27 days |

*Blueing time is defined as the time when the first tinge of blue is noted.

The results again demonstrate that BHT dissolved in varnish has a protective effect on the guaiac paper when coated on the cover of the test slide.

The BHT may be dissolved or suspended in a suitable organic solvent such as acetone or alcohol and applied to the cover flaps. Advantageously, varnish, which is a solution of a resin or drying oil in a volatile solvent, is employed as the carrier for the BHT. The varnish solution is coated or printed on the slide covers and not applied to the guaiac paper.

Preferably solutions or suspensions containing up to five percent by weight of BHT may be employed. Most advantageously, solutions of about 2 to 3 percent are employed.

The following examples are not limiting but are illustrative of this invention.

EXAMPLE 1

| Ingredients | Amounts |
|---|---|
| 2,6 di-tert-butyl-p-cresol (BHT) | 10 gms. |
| Varnish | 454 gms. |

BHT was dissolved in the varnish and printed on the inside cover slides of a 'Hemoccult' test slide.

The varnish was comprised of a phenolic resin, China wood oil, linseed oil, and alcohol.

EXAMPLE 2

| Ingredients | Amounts |
|---|---|
| 2,6-di-tert-butyl-p-cresol (BHT) | 10 gms. |
| Acetone | 454 gms. |

BHT was dissolved in the acetone and coated on the slide cover of a 'Hemoccult' slide.

What is claimed is:

1. A method of stabilizing a specimen slide for occult blood testing having a guaiac treated specimen receiving sheet between a front panel and a rear panel with openings in the front and rear panels and pivotal covers to cover said openings which comprises applying a solution or suspension of 2,6-di-tert-butyl-p-cresol to said pivotal covers.

2. The method of claim 1 in which the solution or suspension is applied to the inside cover of the slide.

3. The method of claim 1 in which the 2,6-di-tert-butyl-p-cresol is in a varnish solution or suspension.

4. The method of claim 1 in which the 2,6-di-tert-butyl-p-cresol is in a solution of acetone.

5. The method of claim 1 in which the 2,6-di-tert-butyl-p-cresol is present from about 2 to about 3 percent by weight.

6. The method of claim 1 in which the solution is printed on the pivotal covers.

* * * * *